(12) United States Patent
Schulz et al.

(10) Patent No.: US 6,580,086 B1
(45) Date of Patent: Jun. 17, 2003

(54) SHIELDED OPTICAL PROBE AND METHOD

(75) Inventors: Christian E. Schulz, Rancho Santa Margarita; Eugene E. Mason, La Mirada; Ammar Al Ali, Tustin, all of CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/420,544

(22) Filed: Oct. 19, 1999

Related U.S. Application Data (60) Provisional application No. 60/150,922, filed on Aug. 26, 1999.

(51) Int. Cl.$^7$ ............................................. G06K 15/00
(52) U.S. Cl. ..................... 250/557; 250/461.2; 128/633
(58) Field of Search ........................... 250/557, 227.14, 250/221, 214.1, 573, 461.2, 338.5, 239; 356/41, 39; 128/633, 665–667

(56) References Cited

U.S. PATENT DOCUMENTS

| | | | | |
|---|---|---|---|---|
| 4,685,464 A | | 8/1987 | Goldberger et al. ........ | 128/633 |
| 5,247,931 A | | 9/1993 | Norwood .................... | 128/633 |
| 5,313,940 A | | 5/1994 | Fuse et al. .................. | 128/633 |
| 5,438,986 A | | 8/1995 | Disch et al. ................ | 128/633 |
| 5,490,523 A | * | 2/1996 | Isaacson et al. ............ | 128/633 |
| 5,939,609 A | | 8/1999 | Knapp et al. ................ | 73/1.01 |

FOREIGN PATENT DOCUMENTS

| | | |
|---|---|---|
| EP | 262 779 | 4/1988 |
| EP | 481 612 | 10/1990 |
| EP | 745 348 | 12/1996 |
| EP | 0 832 598 A2 | 4/1998 |
| JP | 02017462 | 1/1990 |
| JP | 10314149 | 12/1998 |
| JP | 11053662 | 2/1999 |
| JP | 11185193 | 7/1999 |
| WO | 97/23159 | 7/1997 |

OTHER PUBLICATIONS

"Pulse Oximeter 3 and 3i," Minolta, http://www.minoltausa-.com/eprise/main/MinoltaUSA/MUSAContent/ISD/DetailPage?canam, 1 page downloaded and printed from the World Wide Web on Aug. 7, 2002.
"PULSOX Sensors," Minolta, http://www.pulsoxminolta.ch/probeslhtm, 4 pages downloaded and printed from the World Wide Web on Aug. 7, 2002.

* cited by examiner

Primary Examiner—Que T. Le
(74) Attorney, Agent, or Firm—Knobbe, Martens, Olson & Bear, LLP (57) ABSTRACT

An optical probe, which is particularly suited to for use in measurements on tissue material of a patient. In one embodiment, the probe comprises upper and lower housing elements incorporating a light energy source and corresponding detector. The tissue material of the patient is disposed between the upper and lower housing elements such that the light energy emitted by the source passes through the tissue material to the detector. A plurality of light shields are attached to one or both of the housing elements to reduce the amount of ambient and reflected light reaching the detector. Additionally, various portions of the upper and lower housing elements and shields utilize light absorbent coloration and/or coatings which further mitigate the effects of undesired ambient and reflected light, thereby reducing noise generated within the instrument and increasing its accuracy. In one embodiment, the light shields are made removable from the optical probe, thereby facilitating replacement. A circuit for monitoring the condition of the probe, and indicating when replacement of the probe is desirable, is also disclosed.

36 Claims, 11 Drawing Sheets

SHIELDED OPTICAL PROBE AND METHOD

This application claims the benefit of earlier filed provisional patent application Ser. No. 60/150,922, filed Aug. 26, 1999.

BACKGROUND OF THE INVENTION

1. Field of the Invention

The present invention relates to low-noise optical probes which may be used to sense optical energy passed through or reflected from a medium to determine the characteristics of the medium.

2. Description of the Related Art

The physical characteristics of a given medium may often be determined by transmitting electromagnetic or acoustic energy through, or reflected energy from, portions of the medium. For example, in the context of medical diagnosis, light or sound energy may be directed onto a portion of a patient's body, and the fraction of that energy transmitted through (or reflected by) the patient's body measured to determine information about the various physical attributes of the patient. This type of non-invasive measurement is both more comfortable for and less deleterious to the patient than invasive techniques, and can generally be performed more quickly.

Non-invasive physiological monitoring of bodily function is often required. For example, during surgery, blood oxygen saturation (oximetry) is often continuously monitored. Measurements such as these are often performed with non-invasive techniques where assessments are made by measuring the ratio of incident to transmitted (or reflected) light through an accessible part of the body such as a finger or an earlobe. A typical transmissive non-invasive monitoring device includes a light source such as a light-emitting diode (LED) placed on one side of the body part, while a photodetector is placed on an opposite side of the body part. Light energy generated by the LED is transmitted through the tissue, blood, and other portions of the body part, and detected by the photodetector on the other side. Alternatively, in a reflective device, the detector is placed on the same side of the body part as the light source, and the amount of light energy reflected by the body part measured.

The transmission of optical energy passing through the body is strongly dependent on the thickness of the material through which the light passes (the optical path length). Many portions of a patient's body are typically soft and compressible. For example, a finger comprises a number of components including skin, muscle, tissue, bone, and blood. Although the bone is relatively incompressible, the tissue, muscle, and skin are easily compressible or deformed with pressure applied to the finger, as often occurs when the finger is bent. Thus, if optical energy is made incident on a patient's finger, and the patient moves in a manner which distorts or compresses the finger, the optical properties, including optical path length, may change. Since a patient generally moves in an erratic fashion, the compression of the finger is erratic and unpredictable. This causes the change in optical path length to be erratic, making the absorption of incident light energy erratic, and resulting in a measured signal which can be difficult to interpret. Similarly, movement of the patient during a reflective measurement can dramatically affect the quality of the signal obtained therefrom.

In addition to the typical problem of patient movement, the presence of unwanted ambient and/or reflected light energy interferes with the measurement of the intensity of the light transmitted through or reflected by the body part. Optical transmission/reflection systems as described above utilize a light energy detector which measures, inter alia, the intensity of light transmitted to or reflected from the body part being analyzed. Since ambient light incident on the detector affects the intensity measurement, noise or error is introduced into the measured signal by such ambient light. Similarly, light generated by the light source within the measuring device (typically, an LED) which is not transmitted through or reflected by the body part under examination will also result in signal error if such light is received by the detector. These "secondary" reflections arise when light emitted by the light source is reflected by structures within the optical probe onto the detector. Accordingly, to increase the accuracy of the measurement process, both ambient light and "secondary" reflections from the light source should be mitigated.

Figure 1A:
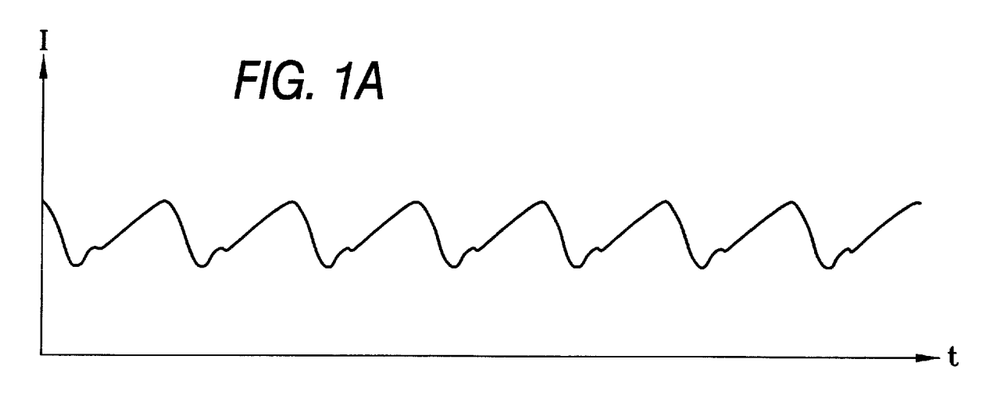
FIG. 1a illustrates an ideal optical transmittance signal that would be measured by a typical prior art optical probe when utilized for blood oximetry.
Figure 1B:
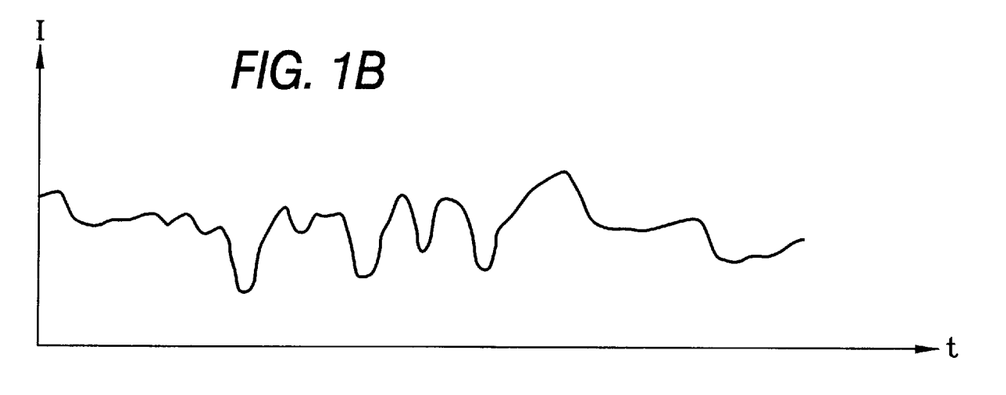
FIG. 1b illustrates a non-ideal optical transmittance signal measured by a typical prior art optical probe when utilized for blood oximetry.

FIG. 1a illustrates an ideal signal waveform obtained from an optical probe system. FIG. 1b illustrates an actual spectra obtained from a typical optical probes not corrected for the effects of patient motion or ambient/reflected light. Note the significant increase in noise (and resulting loss of signal clarity) in FIG. 1b due to these effects.

Prior optical probes have successfully addressed the issue of ease of use and patient motion during measurement. See, for example, U.S. Pat. No. 5,638,818 entitled "Low Noise Optical Probe," assigned to the Applicant herein, which discloses a system utilizing a chamber which isolates that portion of the patient's tissue under examination from compression or movement by the patient. The device is attached to the finger of a patient, thereby readily and accurately positioning the tissue of the patient's finger over the chamber.

However, attempts at limiting the effects of ambient and "secondary" reflected light have been less successful, not due to their ineffectiveness, but rather due to their obtrusiveness and relative complexity of use. A need exists, especially in the health care context, for a simple, fast, unobtrusive, and largely error-free means of non-invasive measurement of a patient's physical parameters. Especially critical is the attribute that such means be easily adapted to a variety of different patient types and characteristics with little or no adjustment, as is the device disclosed in the aforementioned patent. Prior art methods of mitigating ambient and reflected light interference have involved coverings or shrouds which substantially envelop the optical probe and tissue, thereby requiring substantial sizing and adjustment of the covering for each different patient being measured. Another disadvantage of such methods is that the placement of the patient's appendage (such as a finger) in relation to the light source and detector can not be reliably verified by the person administering the measurement unless the probe is first placed on the appendage, and the covering installed thereafter, or alternatively, unless the patient is queried. This necessitates additional time and effort on the part of the patient and the person making the measurement.

Another factor relating to the efficacy of an optical probe is force distribution on the body part or tissue material being measured. Specifically, if force is distributed on the tissue material being measured unevenly or disproportionately, varying degrees of compression of the tissue may result, thereby producing a broader range of optical path lengths in the region of the light source and detector. Furthermore, if the force that the probe exerts on the tissue material is highly localized, the ability of the patient to move the tissue material with respect to the source/detector is enhanced, thereby leading to potentially increased noise levels within the signal generated by the probe.

Yet another consideration relating to non-invasive optical probe measurement involves cost. In recent times, the demand has increased significantly for both disposable and reusable optical probes which are suitably constructed to provide accurate, low-noise measurements. The aforementioned prior art methods of attenuating ambient and reflected light employing coverings or shrouds carry with them a significant cost, especially if the probe (or components thereof) must be replaced on a frequent basis. Therefore, in many applications, it would be useful to have a low-cost reusable optical probe capable of attenuating ambient and reflected light, with only the degradable components being easily and cost-effectively replaced as required, without necessitating the replacement of the entire probe. Similarly, it would be useful to have a disposable probe capable of attenuating ambient and reflected light, which could be routinely replaced in its entirety a cost-effective manner.

Finally, existing optical probes do not include an easy to use and reliable means for determining when to replace the probe. At present, the probe operator or health care provider must keep a record or log of the date of installation of a given probe, and replace it at a given periodicity or simply replace the probe when it seems worn out. This approach is problematic, however, not only from the standpoint of additional time and effort consumed in maintaining the record, but more significantly from the perspective that the measurement of installed time is not necessarily representative of the wear on the probe. For example, two probes installed on the same date may experience significantly different levels of wear, depending on the level of use. Alternatively, the operator could keep a log of usage, but this is too burdensome and time consuming.

Based on the foregoing, a need exists for an improved low-noise optical probe which (i) is simple in design and easy to use under a variety of different operating conditions; (ii) is capable of attenuating ambient and reflected light without necessitating probe adjustment or fitting to each different patient; (iii) is capable of alerting the operator when replacement is required; and (iv) is cost effective. Such an improved probe would also ideally shield against noise caused by electromagnetic interference (EMI).

SUMMARY OF THE INVENTION

The present invention satisfies the foregoing needs by providing an improved optical probe for use in non-invasive energy absorption or reflection measurements, as well as a method of using the same.

In a first aspect of the invention, an improved shielded optical probe assembly is disclosed which incorporates a light energy source and light energy detector embedded within a multi-part housing adapted to receive and clamp onto tissue material from the patient. When the probe is operating, light energy is directed from the light energy source through a first aperture formed within a first element of the housing and onto the tissue material of the patient, which is received within the probe. A portion of this light is transmitted through (or reflected from) the tissue material onto the detector via a second aperture. In this fashion, a light generated by the light source and transmitted through or reflected from the tissue material at a localized point is received by the detector. A light shield is fitted to the housing so as to partially surround the tissue material when it is received within the housing, thereby attenuating ambient light incident on the optical probe. In one embodiment, the light shield is made removable in order to facilitate its replacement after degradation and wear. Additionally, portions of the shield and housing are colored and/or coated such that light incident on these portions is absorbed or attenuated. The foregoing light attenuation features act to reduce the effects of noise induced within the detector (and associated processing circuitry) due to light energy not transmitted directly through or reflected from the tissue material from the light source. The probe is also optionally fitted with a diffraction grating and Faraday shield to mitigate the effects of unwanted optical modes and electromagnetic interference on probe accuracy.

In a second aspect of the invention, the foregoing optical probe includes a mechanism for equalizing the force applied to the tissue of the patient when the probe is clamped thereon. In one embodiment, a series of elongated apertures each receive hinge pins which are biased apart by springs wound around the axis of the pins. When the housing elements of the probe are grasped and compressed together by the user, the hinge pins are forced against one edge of the elongated apertures, thereby providing a fulcrum for opening the probe. After the probe is opened, and the patient's finger inserted, the compressing force is removed, thereby allowing the housing elements to clamp onto the finger. As the compression force is removed, the spring bias allows the previously compressed ends of the housing elements apart, and urging the pins to the opposite edge of the elongated apertures, and "leveling" the housing elements into a more parallel orientation. This parallel orientation distributes force on the patient's finger more evenly.

In a third aspect of the invention, a monitoring device is disclosed which is integrated with the optical probe circuitry in order to assist the operator in determining when to replace the probe. In one embodiment, the monitoring device is a counter which counts the number of electrical pulses generated by the detector circuitry, and correlates this number to the time of actual probe operation and percent of useful lifetime. A light emitting diode visible on the exterior of the probe is used to alert the operator to the need for probe replacement.

In another aspect of the invention, a method of measuring the amount of light transmitted or reflected by the tissue material of a patient using the aforementioned optical probe is disclosed. In one embodiment of the method, the tissue material is inserted into the shielded probe housing, and light generated by the light source of the probe is transmitted via the first aperture into the tissue material. Light energy transmitted (or reflected) by the tissue material is then detected by the detector via the second aperture, and a signal relating to the intensity of the detector generated. Ambient light incident on the probe, and light generated by the light source and scattered off components other than the tissue material, are attenuated or absorbed by the shield and absorptive coating(s) during detection and signal generation in order to reduce any noise component associated therewith. The operating time of the probe is also counted in order to monitor probe remaining lifetime.

DETAILED DESCRIPTION OF THE INVENTION

The invention is described in detail below with reference to the figures, wherein like elements are referenced with like numerals throughout.

It is noted that the term "tissue material" as used herein includes, without limitation, the skin, tissue, blood, cartilage, ligaments, tendons, muscle, or bone of a given portion of a patient's body, such as the distal end of a finger, or any portion thereof.

The term "light energy" as used herein refers to any type of electromagnetic radiation or energy, whether comprised of a narrow, discrete frequency or multiple frequencies. Examples of light energy include visible light, infrared radiation, and ultraviolet radiation. While described as an "optical" probe, the invention disclosed herein may also feasibly be used in conjunction with other forms of energy or radiation, whether optically visible or not.

Figure 2:
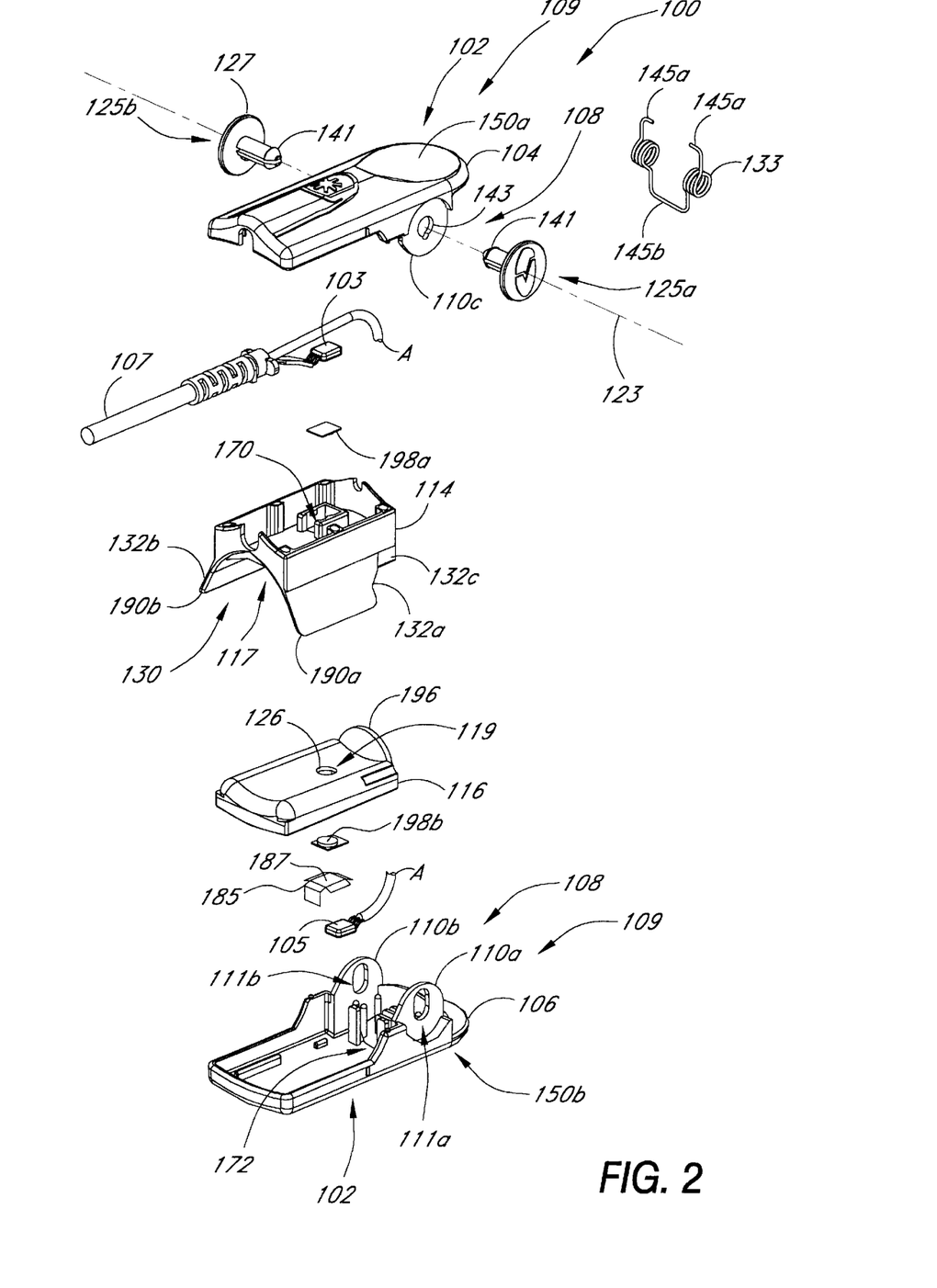
FIG. 2 is an exploded perspective view of a first embodiment of the optical probe of the present invention, configured to measure optical transmission.
Figure 3:
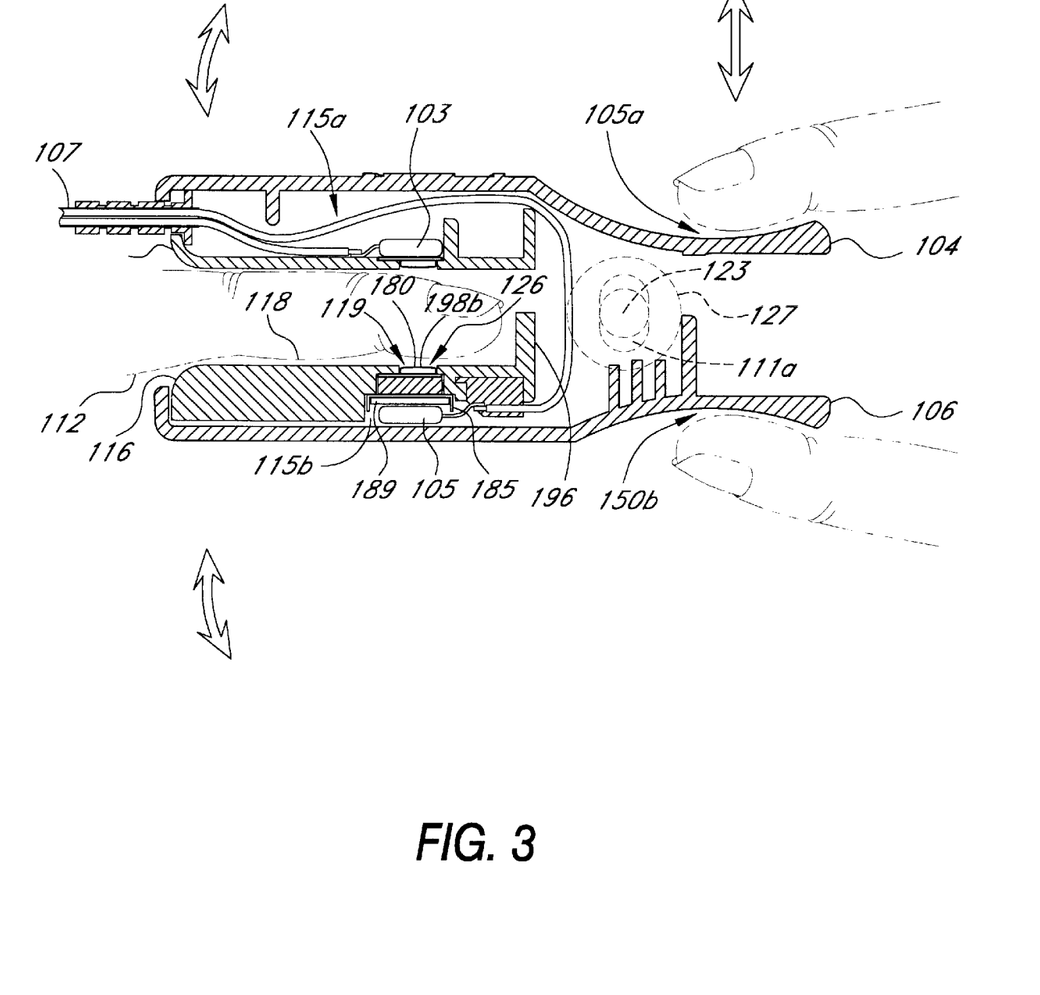
FIG. 3 is a cross-sectional view of the optical probe of FIG. 2 when assembled, taken along line 3—3 thereof.

As shown in FIGS. 2 and 3, a first embodiment of the improved optical probe of the present invention is described. As shown in FIGS. 2 and 3, the present embodiment of the probe 100 generally comprises a two-piece housing 102, a light energy source 103, and a light energy detector 105, and an electrical supply and signal cable 107. The housing 102 consists of a first (upper) housing element 104 and a second (lower) housing element 106, which are rotatably attached to one another via a pivot element 108. The light source 103 is disposed within the upper housing element 104, while the detector is disposed within the lower housing element 106. The housing 102 of the present embodiment is adapted to receive the distal end of a finger 112 as shown in FIG. 3, with the "upper" housing element 104 engaging the upper surface 113 of the finger 112, and the "lower" housing element 106 engaging the lower surface 118 of the finger 112. It will be recognized, however, that the probe 100 may be used in any orientation, such as with the first housing element 104 being located below the second housing element 106. Furthermore, the light source 103 may alternatively be placed in the lower housing element 106, and the detector in the upper housing element 104 if desired, subject to modification of other probe components as described further below. It is also noted that while the following discussion describes a series of exemplary embodiments based on measuring the optical characteristics of a finger 112, the present invention may be adapted for use with any number of other body parts, such as earlobes or loose skin, with equal success. Hence, the specific embodiments described herein are merely illustrative of the broader invention.

The first and second housing elements 104, 106 of the probe 100 of FIGS. 2 and 3 are generally rectangular in form, with the pivot element 108 being disposed near a common end 109 of each of the elongate housing elements 104, 106. The housing elements 104, 106 are in the present embodiment formed from an opaque plastic using an injection molding process of the type well known in the polymer sciences, although other materials and formation techniques may be used. The first housing element 104 includes a monitoring light emitting diode (LED) 426 visible to the operator, as is described in greater detail below with respect to FIG. 8. The first and second housing elements 104, 106 further each include support surface elements 114, 116, and one or more pairs of vertical risers 110a–110d with pin apertures 111a, 111b, the latter which are used to form the basis of the pivot element 108. The two housing elements 104, 106 are biased around the rotational axis 123 of the pivot element 108 by a biasing element, in this case a hinge spring 133 as described further below.

Figure 4:
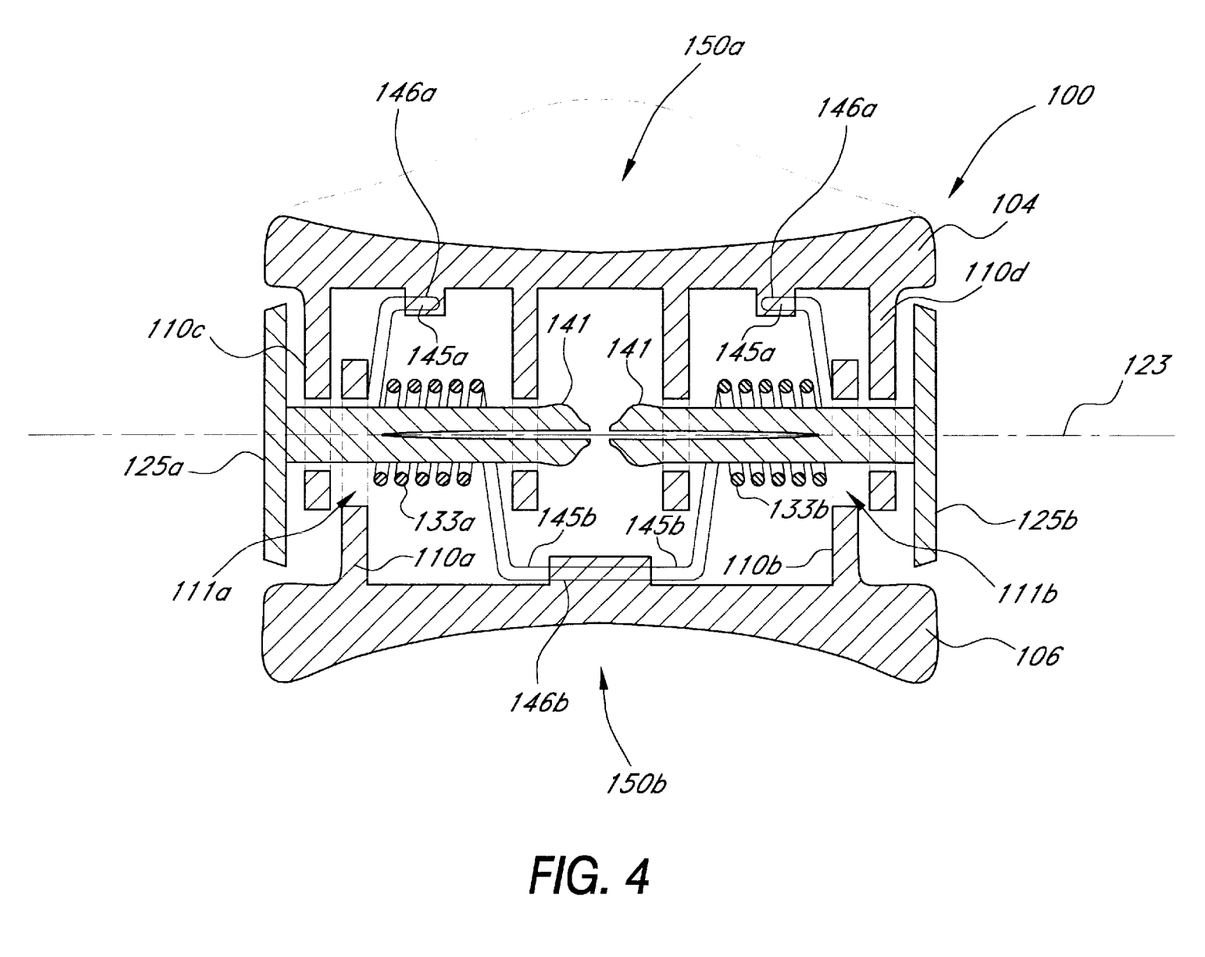
FIG. 4 is a cross-sectional view of the optical probe of FIG. 2 when assembled, taken along line 4—4 thereof.

As shown in FIG. 2, the pivot element 108 of the present embodiment comprises a hinge, and includes the aforementioned vertical risers 110a–110d, two hinge pins 125a, 125b, and biasing spring 133 located along the central axis 123 of the hinge pins 125a, 125b. The hinge pins 125a, 125b each include an outward retaining element 127, and are of a "split pin" design such that a ridge 141 located on the distal end 144 of each pin 125 engages a corresponding edge 143 of the respective interior vertical riser 110c, 110d of the upper housing element 104 when each pin 125 is fully received within the probe 100, as shown in FIG. 4. This arrangement, specifically the ridges 141 of the pins 125 engaging the edges 143 of their respective vertical risers 110 under an outward biasing force generated by the split in the pin, permits the pins 125 to be readily "snapped" into the apertures 111 within the vertical risers 110, thereby forming a hinge with pivot or rotational axis for the upper and lower housing elements 104, 106. The biasing spring 133 fits around the pins 125a, 125b as shown in FIG. 4, the two free ends 145a, and the connecting section 1456 being received with respective holders 146a, 146b formed within the interior surfaces of the upper and lower housing elements 104, 106, respectively. Using this arrangement, the biasing spring 133 is preloaded (i.e., partially wound) so as to bias the upper housing element 104 against the lower housing element 106. A pair of finger recesses 150a, 150b are formed within the outward portion of each of the housing elements 104, 106, at a location between the common end 109 of each housing element and the pivot axis 123, thereby permitting the user to grasp the probe 100 between his or her fingers using the recesses 150a, 150b and separate the probe housing elements 104, 106 by applying force counter to the spring biasing force. In this fashion, the user simply grasps the probe 100, opens it by applying a light force with the grasping fingers, and inserts the distal end of the patient's finger 112 into the opened end 154 of the probe.

As depicted in FIG. 2, the pin apertures 111 of the lower housing element 106 are somewhat elongated in the vertical direction (i.e., in a direction normal to the plane of the housing element 106). This feature has the practical effect of making the upper and lower housing elements 104, 106 conform more readily to the shape of the patient's finger 112 when the latter is received within the probe 100. Specifically, the elongated pin apertures allow the portion of the patient's finger 112 inserted into the open end 154 of the probe (FIG. 3) to act as a fulcrum for a "separating" force generated by the biasing springs 133 such that the common ends 109 of the upper and lower housing elements 104, 106 are forced apart by, inter alia, the bias spring separating force. This separating force is generated by the offset 160 of the bias spring ends 145*a*, and connecting section 145*b* from the axis 123 of the spring, as shown in FIG. 3. When the user grasps the recesses 150 of the housing elements 104, 106 and squeezes, the pins 125 are forced to the fully compressed position within the elongated pin apertures 111; that is, the pins are forced against the bottom edge of the elongated apertures 111 in order to allow the probe 100 to be opened. However, once the finger 112 is inserted into the probe, the disproportionate compression of the finger 112 (due to the interaction of the angled housing elements 104, 106 and the substantially cylindrical finger 112) and the aforementioned bias spring separating force, act to force the common end 109 of the probe housing elements 104, 106 apart, thereby making upper and lower housing elements 104, 106 more parallel to each other as shown in FIG. 3. This "dislocation" of the upper element 104 with respect to the lower element 106 allows more of the surface area of the upper and lower support surface elements 114, 116 (described below) to contact the finger 112, and for more even pressure distribution thereon.

Figure 2A:
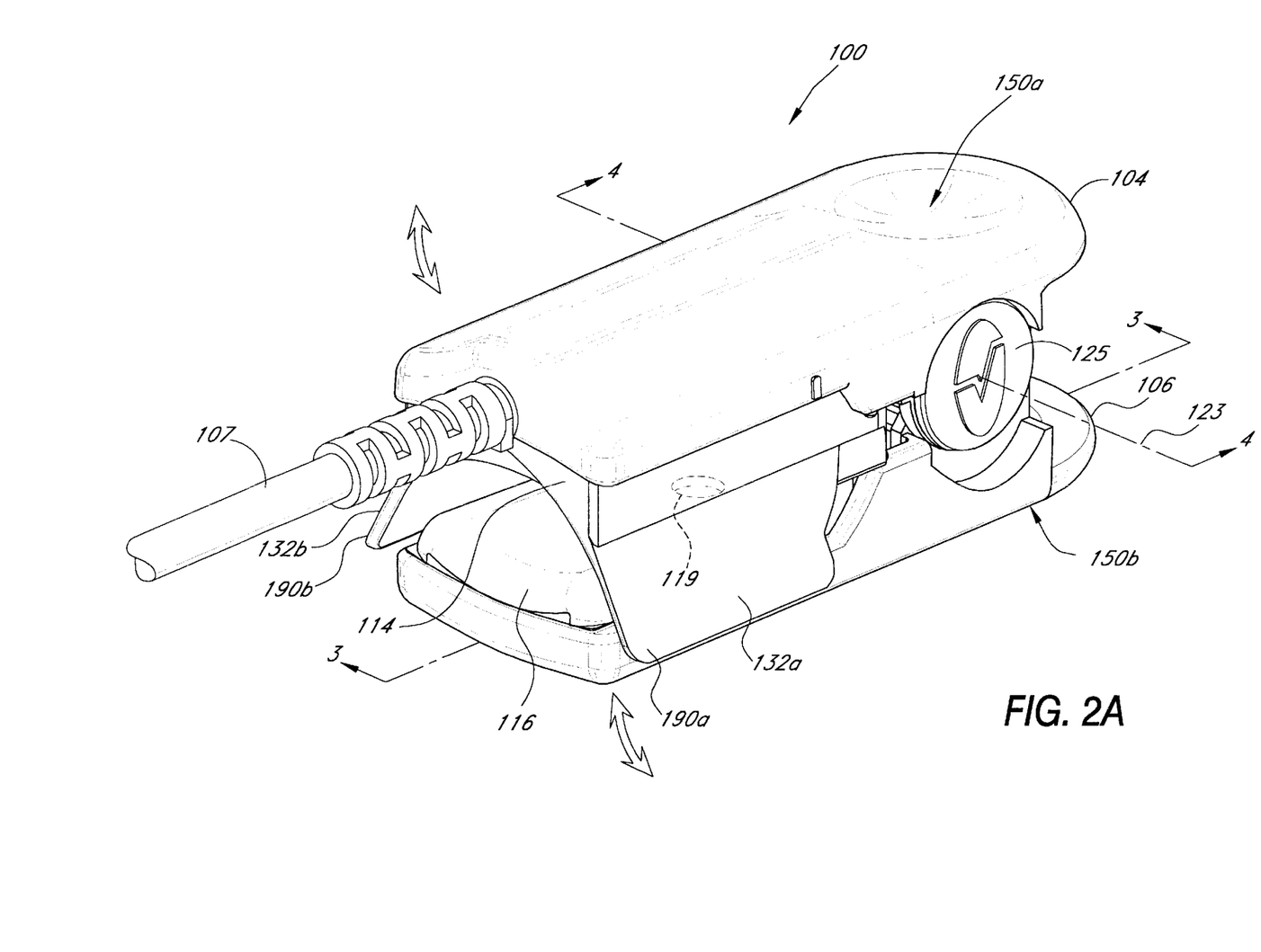
FIG. 2a is a perspective view of the optical probe of FIG. 2 when assembled.

As previously discussed, the housing elements 104, 106 are adapted to receive first (upper) and second (lower) support surface elements 114, 116, respectively, which provide support and alignment for the tissue material, such as the finger 112 shown in FIG. 3, when the probe 100 is clamped thereon. When assembled as in FIGS. 2*a* and 3, the housing elements 104, 106 and support surface elements 114, 116 form interior cavities 115*a*, 115*b* within the upper and lower housing elements 104, 106, respectively, which contain, inter alia, the light source 103 and photodetector 105 as described in greater detail below. The upper support surface element 114 is fashioned from a substantially pliable polymer such as silicone rubber, so as to permit some deformation of the element 114 when in contact with the fairly rigid upper portion 113 of the patient's finger 112. In one embodiment, the upper element 114 is constructed as a membrane of polymer. The lower surface element 116 is fashioned from a substantially solid and rigid (i.e., higher durometer) polymer. This harder, solid polymer is used for the lower surface element 116 since the lower portion of the finger 112 is generally more fleshy and deformable, thereby allowing the skin and tissue material thereof to deform and contour to the shape of the inner region 122 of the lower surface element.

The upper and lower surface elements 114, 116 also include first and second apertures 117, 119, respectively, which communicate with the patient's tissue material when the finger 112 is inserted in the probe 100. The apertures allow for light energy to be transmitted between the light source 103 and tissue material, and similarly between the tissue material and detector 105. The first aperture 117 is also axially located with the second aperture 119 in the vertical dimension, such that when the probe 100 is in the closed configuration with the patient's finger 112 disposed between the upper and lower surface support elements 114, 116, light emitted by the light source 103 through the first aperture 117 is transmitted through the finger 112 and the second aperture 119 and received by the detector 105. Hence, the light source 103, first aperture 117, second aperture 119, and detector 105 are substantially axial in this configuration.

The lower support element 116 is further provided with a positioning element 196 disposed near the pivot element 108 and common end 109 of the probe 100, as shown in FIGS. 2 and 3. The positioning element 196 is oriented vertically with respect to the lower support element 116 so as to stop the distal end of the patient's finger from being inserted into the probe past a certain point, thereby facilitating proper alignment of the finger 112 within the probe 100, especially with respect to the source and detector apertures 117, 119. While the present embodiment uses a semi-circular tab as the positioning element 196, it will be recognized that other configurations and locations of the element 196 may be used. For example, the tab could be bifurcated with a portion being located on the upper support surface element 114, and a portion on the lower support surface element 116. Alternatively, the positioning element could be in the form of a tapered collar which receives, aligns, and restrains only the distal portion of the patient's finger. Many such alternative embodiments of the positioning element are possible, and considered to be within the scope of the present invention.

As further described below, the lower surface element 116 optionally includes a chamber 126 coincident with the second aperture 119 to assist in mitigating the effects of patient movement during light transmission or reflection. The structure of such chambers is described in detail in U.S. Pat. No. 5,638,818, entitled "Low Noise Optical Probe", which is incorporated herein by reference. In general, the chamber 126 acts to isolate a portion of the tissue material directly over the chamber 126 and aperture 119, thereby reducing compression of that tissue during movement. This tends to stabilize the signal generated by the detector 105, since the optical transmission path through the tissue material is effectively stabilized and constant. The chamber 126 is deep enough that the detector 105 and the bottom of the chamber 126 do not come into contact with the easily compressible portion of the tissue material, even when the tissue material is caused to move. The movement of venous blood due to compression is also minimized in the field of view of the detector 105.

In the embodiment of FIGS. 2–4, the light source 103 is comprised of one or more devices such as semi-conductive light emitting diodes (LEDs), although it will be appreciated that other light generating devices may be used. The light source 103 may be chosen to emit light at a single known discrete wavelength, at multiple discrete wavelengths, or across a portion of the spectrum (such as that emitted by a "white light" LED), depending on the needs of the particular application. In the present embodiment, the light source 103 consists of two diodes emitting light energy in the infrared and red regions of the electromagnetic spectrum, and a parallel resistor (or resistors) used for security. The construction and operation of such light source drive circuitry is described in U.S. Pat. No. 5,758,644 incorporated herein by reference.

As shown in FIG. 2, the light source 103 is affixed in a recess 170 formed in the interior portion of the upper support surface element 114, and aligned with the aperture 117 formed within the upper support surface element 114. An adhesive such as a UV-cured silicone-based gel is used to affix the LED 103 to the recess 170, although other adhesives or attachment schemes may be employed. The light energy detector 105, in the present case a semi-conductive photodetector, is received within a corresponding recess 172 within the lower support surface element 116. As with the LED 103, the photodetector 105 may be fixed within its recess 172 according to a number of different methods, including but not limited to adhesive, a press fit, or clear epoxy resin which transmits light over a range of wavelengths of interest.

As illustrated in FIG. 2, the upper support surface element 114 further includes an optical energy shield 130 which, in the present embodiment, is comprised of a plurality of shield tabs 132a, 132b, 132c which protrude from the upper support surface element 114. The shield 130 and tabs 132a, 132b, 132c are sized and shaped so as to conform substantially to the outer circumference of the patient's finger 112, providing at least a partial seal against ambient light incident on the probe exterior and otherwise exposed portions of the finger 112. Since the shield 130 is also formed from the same pliable polymer as the first support surface element 114, both the shield and upper support surface element are capable of automatically adapting their shape substantially to that of the patient's finger 112 without further adjustment. Specifically, as the probe 100 is closed around the finger 112, the central region of the pliable upper support surface element 114 engages the more rigid upper portion of the patient's finger, thereby compressing the element 114 in this region. This tends to draw the proximal portions 190a, 190b of the shield tabs 132a, 132b, 132c toward the finger 112, thereby forming a better seal. In this fashion, patients having fingers of different circumferences can be accommodated with the same probe shield 130.

As shown in FIGS. 2 and 3, the present embodiment of the optical probe 100 includes optional optically transparent covers 198a, 198b which are fitted at least partly within the apertures 117, 119 formed in the upper and lower support surface elements 114, 116, respectively. The covers 198a, 198b are fabricated from a rigid or semi-rigid transparent polymer (such as polycarbonate), although other materials may be substituted. The two covers 198a, 198b act as protection for the source 103 and detector 105 disposed thereunder, respectively. Specifically, the covers 198 are bonded to the interior surface of the upper and lower support surface elements 114, 116 such that the outer surfaces 199a, 199b of the covers 198 are essentially flush with the outer surfaces of their respective support surface elements 114, 116. The outer surfaces 199a, 199b (FIG. 3) of the covers 198a, 198b may also be curved or contoured if desired. It is further noted that while the present embodiment utilizes covers 198 which are optically transparent, the physical and optical properties of the covers may be adjusted to produce the desired characteristics. For example, one or both of the covers 198a, 198b may include a scattering medium as described further below.

In an alternative embodiment, the windows for the emitter and detector are filled with a UV-cured silicone that is transparent to the wavelengths of the emitter, and the transparent covers described above are not used.

In addition to the aforementioned features, the upper and lower support surface elements 114, 116 and light shield 130 are advantageously formed from or coated with a light absorbing material which further mitigates the effects of ambient light, as well as stray (i.e., "secondary") reflected light within the probe generated by the light source 103. Specifically, light generated by the light source 103 can take several paths in reaching the detector, only one of which is the desired path via the aforementioned first and second apertures 117, 119 and through the interposed tissue material. Preferably, in order to obtain more accurate measurement of transmitted light intensity, these other paths are eliminated or attenuated. Hence, in one embodiment, the light absorbing material is disposed on the entire upper and lower surface elements 114, 116 and shield 130 so as to substantially absorb any secondary reflections prior to being received by the detector 105. In the embodiment of FIGS. 2–4, the upper surface element 114 (and integral shield 130) and lower surface element 116 may be formed from a black, opaque material which both inhibits the transmission of light energy through its thickness and absorbs at least a portion of the incident light incident onto its surface. In this fashion, the absorbing material mitigates the effects of both reflections transmitted from the light source 103, and ambient light incident on the surface elements 114, 116. It will also be appreciated that while the present embodiment employs surface elements 114, 116 which are formed from an opaque material, absorptive coatings or coverings may be used as well. For example, all or a portion of the upper and lower surface elements 114, 116 and shield 130 could be coated with a light-absorbing paint or other absorbing substance as an alternative to or in addition to the use of the aforementioned opaque material. In one embodiment, the elements 114 and 116 are white or reflective in the vicinity immediately surrounding the apertures 117, 119.

Figure 2B:
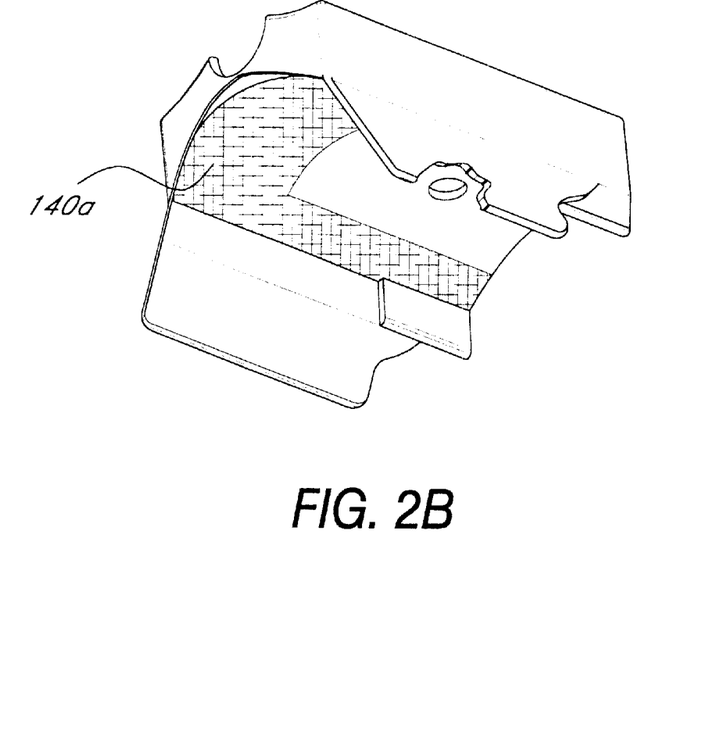
FIG. 2b is a perspective view of an upper support surface element of the optical probe of the present invention with a nonreflecting portion depicted with shading.
Figure 2C:
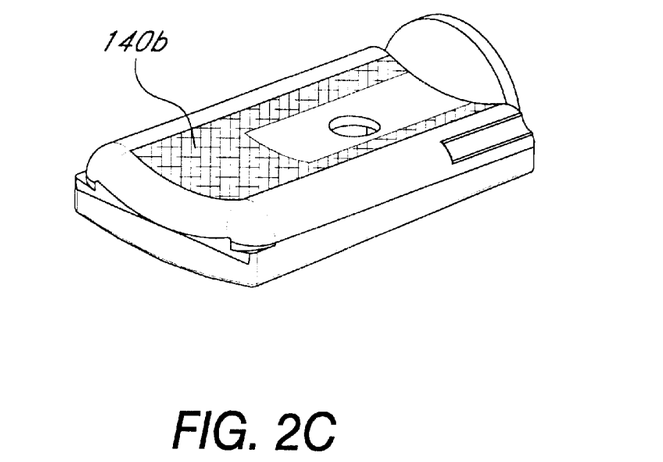
FIG. 2c is a perspective view of the lower support surface element shown in FIG. 2 with a nonreflecting portion depicted with shading.

For example, FIGS. 2b and 2c depict one embodiment of the upper and lower elements 114, 116, showing nonreflective surfaces 140a and 140b with shading. In this embodiment, the area directly around the apertures for the LED and photodetector remain white or reflective to promote light transmission in the area of the photodetector.

Figure 5:
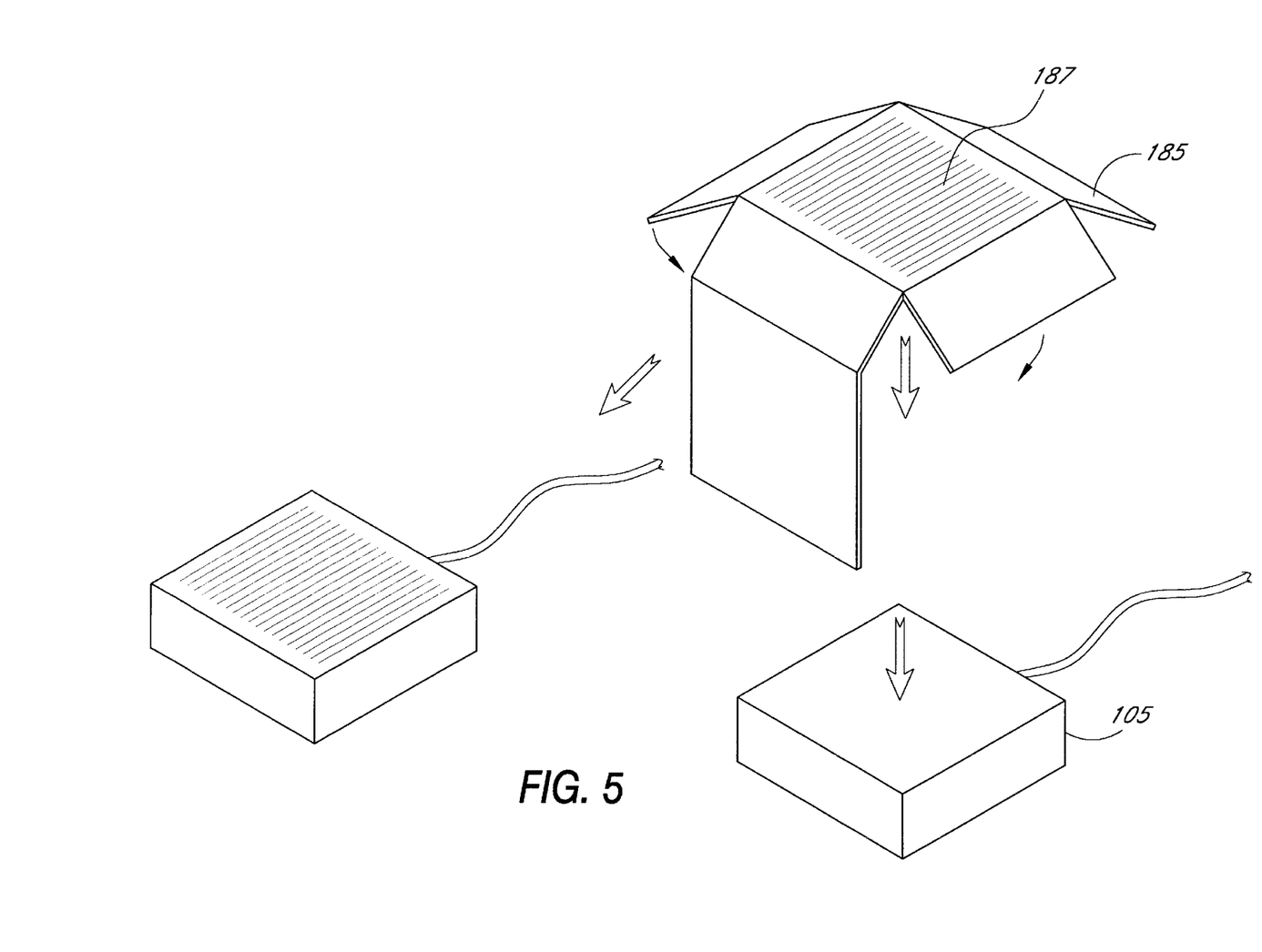
FIG. 5 is a perspective view of the detector shield of the present invention, shown during assembly.

In addition to the light shield and absorptive materials described above, the present embodiment utilizes an electromagnetic noise shield 185 as illustrated in FIG. 5. The noise shield 185 operates on Faraday principles to block or attenuate electromagnetic interference (EMI). The noise shield 185 has a grating 187 which permits light to pass while still blocking electromagnetic energy. In a preferred embodiment, this is a very fine screen with a large open percentage to permit as much light as possible yet still block EMI. In the illustrated embodiment, the detector shield 185 is an etched copper shield made of copper foil approximately 4 mils thick, which is wrapped around the detector 105 in a box-like fashion so as to substantially enclose the detector, significantly insulating it from a external EMI. The screen or grating 187 is etched through the shield to allow light from the light source 103 to transmit through the shield 185 to the detector 105. The noise shield 185 is also electrically grounded to the detector ground, thereby precluding the buildup of electrical charge.

In the optical probe of FIGS. 2–4, the apertures 117, 119 optionally may be filled wholly, or in part, by a scattering medium 180. The scattering of the light energy within a scattering medium has been found to increase the signal-to-noise ratio of the signal generated by the detector. Ideally, the scattering medium 180 scatters but does not significantly absorb light energy at the wavelengths of significance for the operation of the probe. In other words, the material is substantially transparent to optical absorption, but none-the-less effectively scatters light energy. In general, the scattering medium 180 may comprise one of a number of fixotropic substances (i.e., substances having two or more mixed materials which are conducive to scattering). The construction and use of scattering media are further described in the aforementioned U.S. Pat. No. 5,638,818.

Figure 6:
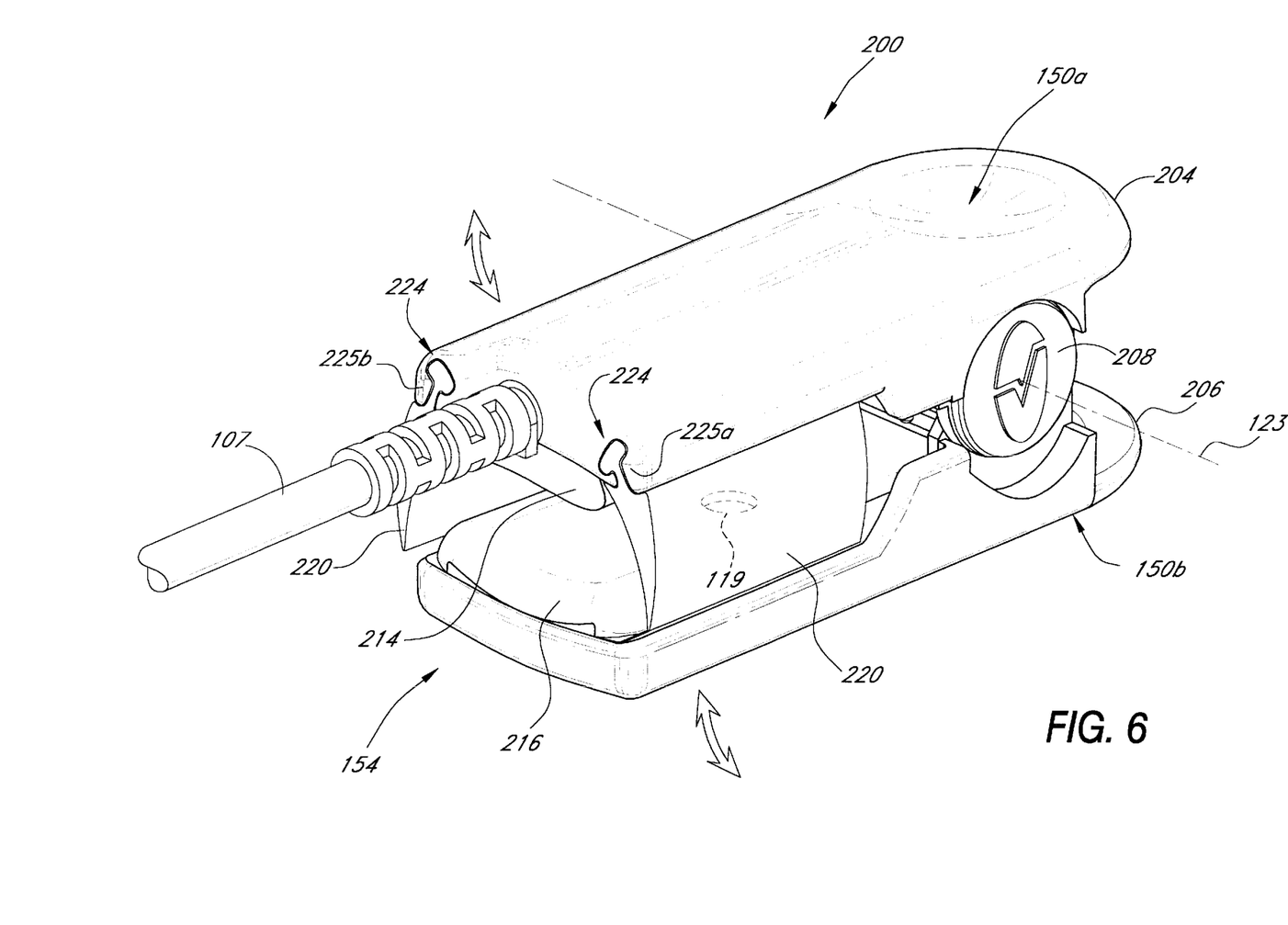
FIG. 6 a perspective view of a second embodiment of the optical probe of the present invention configured to measure optical transmission.
Figure 6A:
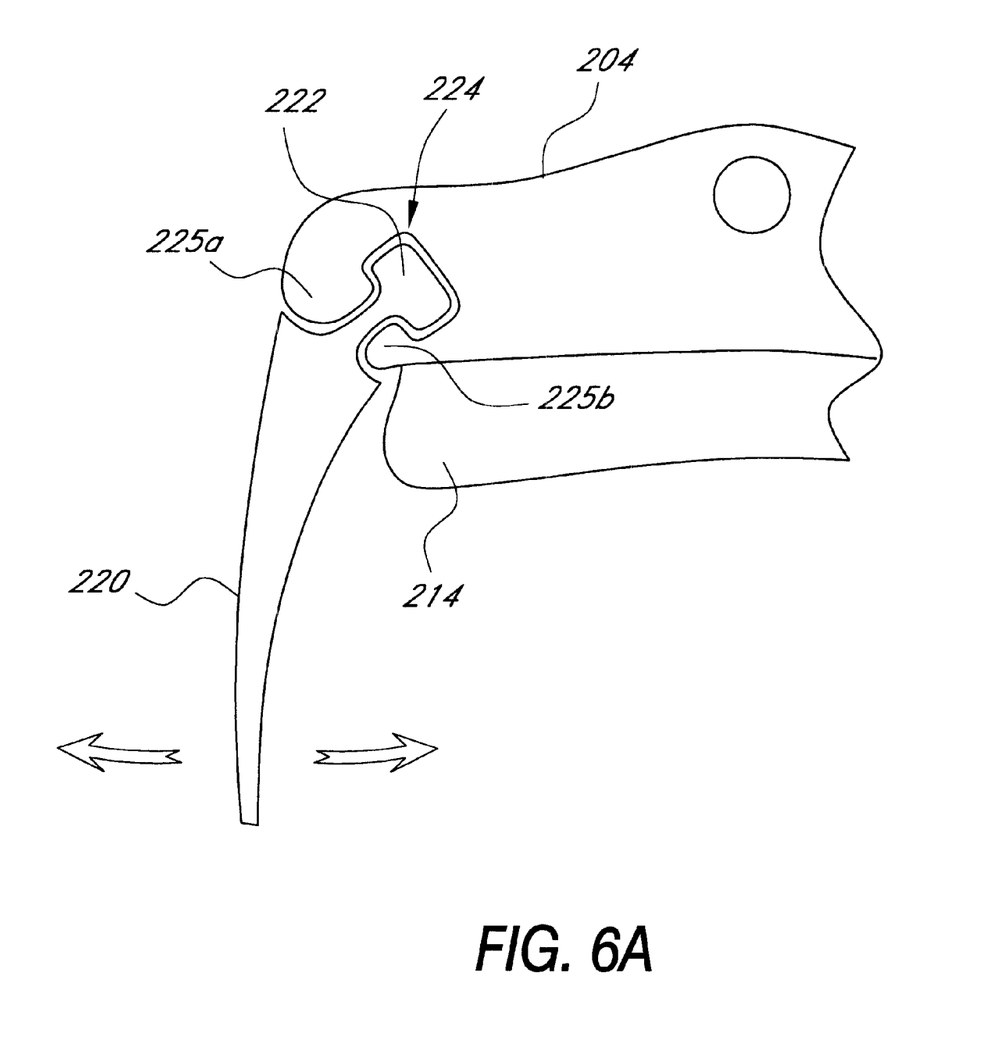
FIG. 6a is a detail plan view of the removable shield elements and channels of the optical probe of FIG. 6.

FIGS. 6 and 6a illustrate a second embodiment of the optical probe of the present invention. As illustrated, this second embodiment of the probe 200 comprises, inter alia, first and second housing elements 204, 206, upper and lower support surface elements 214, 216, and pivot assembly 208 as previously described. The embodiment of FIG. 6 further includes a plurality of discrete, removable shield tabs 220 which are mounted to the optical probe 200 using a sliding key and channel arrangement. Specifically, each of the tab elements 220 are formed such that the edge 222 which engages the optical probe 200 is shaped or keyed so as to fit within the channels 224 located on the outer portions of and running longitudinally along the upper housing element 104 of the optical probe, as shown in FIG. 6a. The present embodiment employs channels 224 and edges 222 which are substantially square in cross-section, although it will be recognized that other cross-sectional shapes including rectangles, polygons, and triangles and circles may be used with equal success. The use of a square (or other shape) for the edges 222 and their corresponding channels 224 prevents significant lateral movement or rotation of the edges 222 in the channels 224 when installed. As shown in FIG. 6a, the channels 224 may be further formed such that a pair of support ridges 225a, 225b act to support the tabs 220 when the latter are inserted into the channels 224, thereby adding additional rigidity to the shield tabs 220. The shield tabs 220 may also be made interchangeable from side to side if desired.

The shield tabs 220 of the embodiment of FIGS. 6 and 6a are fabricated from a somewhat rigid yet flexible polymer such as silicone rubber of durometer 45A. This construction permits their removal from and insertion into the channels 224 of the housing element 204, while allowing some degree of flexibility so as to adapt to the shape and size of each individual patient's finger when the probe is fitted on the patient.

It will be appreciated that while the shield tabs 220 of the present embodiment are mounted using channels disposed along the outer portions of the upper housing element 204, other locations and mounting configurations may be used. For example, the channels 224 could alternatively be located in the lower housing element 206, with the shield tabs 220 extending upward when inserted rather than downward as in FIG. 5. Similarly, the channels 224 could be located within the upper or lower support surface elements 214, 216. Furthermore, retaining mechanisms other than the aforementioned channels 224 may be used, such as pins and corresponding holes, adhesives, or other devices well known in the mechanical arts. In yet another alternative embodiment, the shield tabs 220 could be part of a single component which is received within the channels 224 or other retaining mechanism on the optical probe. A great variety of optical shield configurations according to the present invention are possible, all of which achieve the goals of minimizing noise within the probe 200 while allowing removability of the shield.

Figure 7:
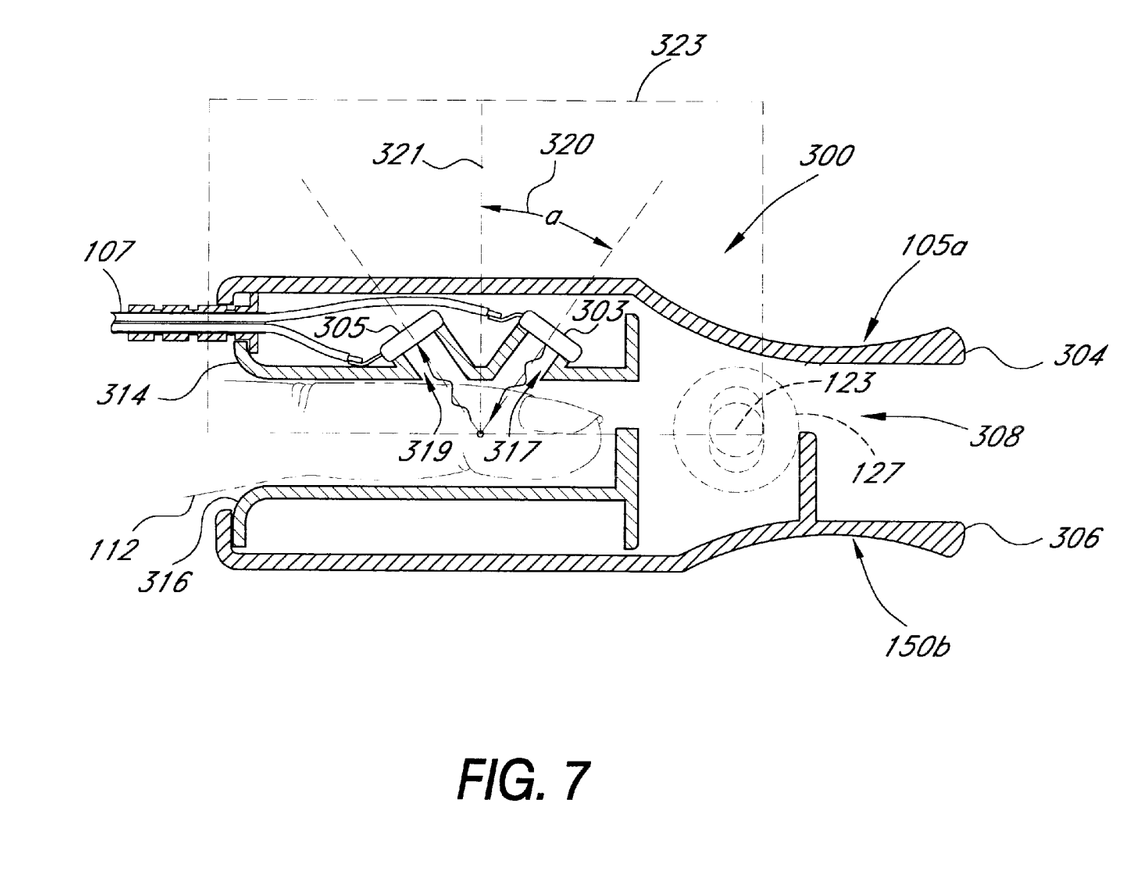
FIG. 7 is a cross-sectional view of a third embodiment of the optical probe of the present invention configured to measure optical reflectance.

As illustrated in FIG. 7, another embodiment of the optical probe of the present invention is described. In this embodiment, the probe 300 includes a light energy source 303 and detector 305, upper and lower housing elements 304, 306, upper and lower support surface elements 314, 316, and pivot element 308, as in the prior embodiment. However, the embodiment of FIG. 7 utilizes the principle of optical reflectance rather than optical transmission; hence, the light source 303 and detector 305 are both co-located within the upper housing element 304, in direct proximity to one another. Source and detector apertures 317, 319 are formed within the upper support surface element 314, their axes being canted at a predetermined angle 320 relative to the normal direction 321 and along a common plane 323. This arrangement permits light to impinge on the surface of the patient's finger 112, be reflected therefrom, and received by the detector 305 via the detector aperture 319.

It will be recognized that while the source 303 and detector 305 and their respective apertures 317, 319 are located generally in the upper housing element 304 and upper support member 314, they may equally as well be located in the lower housing element 306 and support member 316 if desired. Many of such alternative orientations are possible.

Additionally, although the embodiment of FIG. 7 has the axis of the apertures 317, 319 canted at a predetermined angle, such angle is not necessary for the operation of the optical probe. For example, the apertures 317, 319 could alternatively be closely co-located in a vertical orientation; light scattered from various portions of the tissue material of the patient's finger 112 beneath the source aperture 317 would be reflected into the detector aperture 319 and received by the detector 305.

Figure 8:
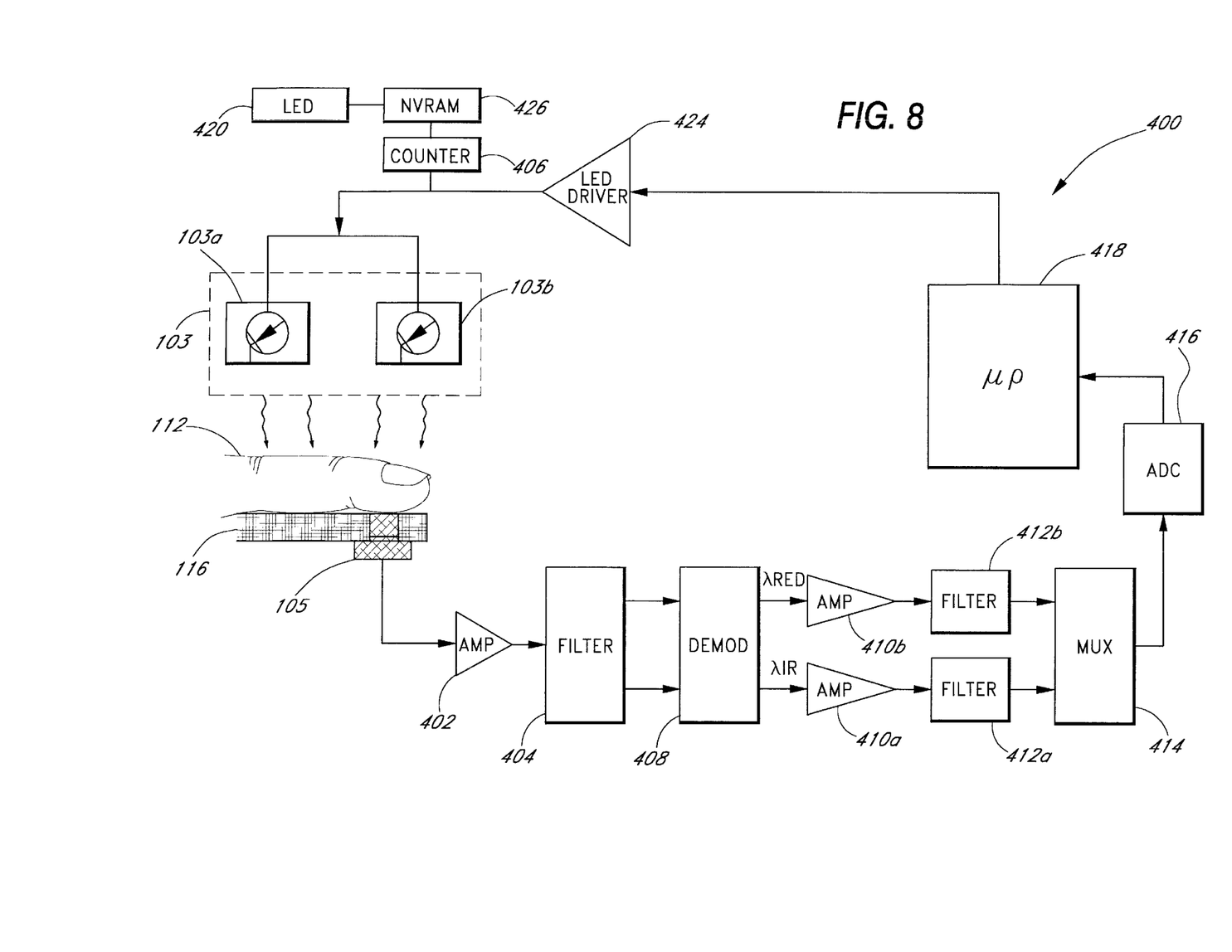
FIG. 8 is a block diagram illustrating one embodiment of a monitoring device circuit according to the present invention.

FIG. 8 illustrates one embodiment of the probe monitoring circuit of the present invention provided with a sensor and a monitor. In this embodiment, the monitoring circuit is comprised generally of a counter 406, non-volatile storage device 420, and monitoring LED 426. Circuitry useful for driving the light source and processing the detector signals is known in the art. The monitoring circuit counts the number of LED activations which is obtained from the modulated drive signals. For example, in one embodiment, the modulated drive pulses to at least one LEDs are also communicated to the counter 406. Specifically, the light source LEDs 103a, 103b are pulsed (modulated) to alternatively emit red and infrared light energy, respectively, as controlled by the LED driver 424 and the microprocessor 418. The drive signals to at least one of the LEDs also clocks the counter 406. In one preferred embodiment, the counter only increments once for a predefined number of activations. In other words, a divide by X circuit forms a portion of the counter. This is because the number of cycles is very high, and a divide circuit reduces the capacity requirements of the counter. The construction and operation of electronic counters are well known in the electrical arts, and accordingly will not be described further. Advantageously, the counter is maintained in a non-volatile RAM (NVRAM) which maintains a running count. When a predetermined number is reached, an LED 426 is activated. This number is determined by, for example, empirical data relating to the longevity of the probe to a given number of detector pulses. The monitoring LED 426 is mounted in the probe housing 102 or remotely from the probe if desired (such as on the probe control module, not shown), and is readily visible to the operator.

It will be recognized that the aforementioned probe monitoring function can be accomplished using a number of different circuit configurations well known in the art. For example, in one alternative embodiment, circuitry is employed which measures the actual time the detector 105 generates an output signal. In another embodiment, the number of pulses applied to each of the LEDs 103a, 103b in the light source 103 is counted. Many other such alternative embodiments are possible.

It will be further recognized that while the circuit of FIG. 8 utilizes an LED 426 for indicating probe age, other indicating devices such as incandescent bulbs, liquid crystal displays (LCDs), or even audio generators may be used.

The pulsed emissions from the LEDs are also detected by the detector 105. The detected signals are amplified by the amplifier 402. The amplified signals are then filtered using a band-pass or other filter 404, thereby passing only that portion of the detected signals corresponding to the desired band of light intensity.

The probe of the present invention may be employed in any circumstance where a measurement of transmitted or reflected energy is to be made, including but not limited to measurements taken on a finger, an earlobe, a lip, or a forehead. Thus, there are numerous other embodiments which will be obvious to one skilled in the art, including but not limited to changes in the shape of the probe and its components, changes in the materials out of which the probe is made, and changes in the shape, dimensions, and location and orientation of the apertures and shield. Furthermore, the probe of the present invention may be employed in measurements of energy or radiation other than light energy as defined herein. Depending upon the type of energy which is most advantageously utilized in a measurement, the type of transmitter or receiver of energy may be changed. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An optical probe for obtaining data from the tissue material of a living organism, comprising:
    an first housing element having a first support surface for supporting said tissue material, and a first aperture formed therein;
    a second housing element having a second support surface and a second aperture formed therein, said second housing element being located proximate to said first housing element and rotatably attached thereto so as to permit said tissue material to be positioned there between;
    a light energy source disposed within said first housing element, said light energy source being positioned such that at least a portion of the light energy emitted is transmitted through said first aperture;
    a light energy detector disposed within said second housing element, said light energy detector being positioned so as to receive at least a portion of said light energy transmitted by said light energy source through said tissue material and said second aperture; and
    a light shield mounted to at least one of said first and second housing elements and located proximate to said tissue material, said light shield attenuating at least a portion of ambient light energy incident on said tissue material,
    wherein at least one of the first support surface and the second support surface includes a first area having a first attenuation property and a second area having a second attenuation property substantially different from said first attenuation property.

2. The optical probe of claim 1, wherein said first and second housing elements are rotatably attached to one another via at least one pivot assembly.

3. The optical probe of claim 2, further comprising a biasing member which biases said first and second housing elements together when said tissue material is received there between.

4. The optical probe of claim 3, wherein said biasing member comprises at least one spring.

5. The optical probe of claim 4, wherein said at least one spring is mounted such that its longitudinal axis is coincident with an axis of said pivot assembly.

6. The optical probe of claim 1, wherein said shield comprises a plurality of shield tabs.

7. The optical probe of claim 6, wherein at least one of said plurality of shield tabs is removably attached to said optical probe.

8. The optical probe of claim 7, wherein said at least one of said plurality of shield tabs is attached to said optical probe using a key and channel arrangement.

9. The optical probe of claim 1, wherein said shield is formed within said first support surface.

10. The optical probe of claim 1, further comprising a chamber having an entrance in the form of said second aperture, wherein at least a portion of said tissue material covers said second aperture and is supported by said second support surface around said aperture, said chamber isolating at least a portion of said tissue material during optical analysis thereof.

11. The optical probe of claim 1, further comprising an optical scattering medium disposed within at least one of said apertures.

12. A method of measuring a physical property using an optical probe, comprising:
    forming a housing element capable of receiving tissue material, said housing element having a first aperture and second aperture formed therein, said first and second apertures being located proximate to said tissue material;
    generating light energy using a light energy source;
    transmitting said light energy through said first aperture onto said tissue material;
    detecting, via said second aperture, at least a portion of said light energy generated by said source and transmitted onto said tissue material, using a detector;
    shielding said detector through at least a partial seal from light energy not generated by said light energy source and not transmitted through said first aperture; and
    absorbing in a first area of the housing element at least a portion of said light energy not generated by said light energy source or not transmitted onto said tissue material;
    reflecting in a second area of the housing element different from the first area, at least a portion of said light energy transmitted onto said tissue material; and
    generating a signal based on said light energy detected by said detector.

13. The method of claim 12, further comprising the act of isolating at least a portion of said tissue material using a chamber formed within said housing element in order to increase the accuracy of said signal.

14. The method of claim 13, further comprising the act of scattering at least a portion of said light energy generated by said optical source and wherein said housing element further includes an optical scattering medium disposed within at least one of said first and second apertures.

15. The method of claim 12, further comprising the act of shielding said detector from electromagnetic interference using a Faraday shield.

16. The method of claim 12, wherein the act of detecting at least a portion of said light energy generated by said source and transmitted onto said tissue material comprises the act of detecting light energy transmitted through said tissue material.

17. The method of claim 12, wherein the act of detecting at least a portion of said light energy generated by said source and transmitted onto said tissue material comprises the act of detecting light energy reflected from the surface of said tissue material.

18. An optical probe comprising:
a housing capable of receiving at least a portion of the tissue material of a patient, said housing having first and second apertures formed therein, said first and second apertures being proximate to said tissue material when said tissue material is received by said housing, at least a portion of said housing comprising an absorptive material capable of absorbing at least a portion of the light energy incident thereon and at least another portion of said housing comprising a reflective material;
a light energy source disposed within said housing, said light energy source being positioned such that at least a portion of the light energy emitted thereby is transmitted through said first aperture onto said tissue material;
a light energy detector disposed within said housing, said light energy detector being positioned so as to receive, via said second aperture, at least a portion of said light energy transmitted onto said tissue; and
a light shield located proximate to said tissue material and at least partially sealing said tissue material from ambient light;
wherein said light shield and said absorptive material of said housing cooperate to attenuate at least a portion of any light energy that was not generated by said light energy source or was generated by said light energy source but was not transmitted through said tissue material when said tissue material is received by said housing.

19. The optical probe of claim 18, further comprising an optical scattering medium disposed at least partly with at least one of said first and second apertures.

20. The optical probe of claim 18, further comprising an electromagnetic shield used to shield said detector from electromagnetic interference.

21. The optical probe of claim 18, wherein said absorptive material is a substantially black coating deposited on at least a portion of said housing element.

22. Data indicative of the physical condition of a patient generated using the method comprising:
forming a housing element capable of receiving tissue material, said housing element having a first aperture and second aperture formed therein, said first and second apertures being located proximate to said tissue material;
generating light energy using a light energy source;
transmitting said light energy through said first aperture onto said tissue material;
detecting, via said second aperture, at least a portion of said light energy generated by said source and transmitted onto said tissue material, using a detector;
shielding said detector using at least a partial seal against light energy not generated by said light energy source and not transmitted through said first aperture;
absorbing in a first area of the housing element at least a portion of said light energy not generated by said light energy source or not transmitted onto said tissue material;
reflecting in a second area of the housing element different from the first area, at least a portion of said light energy transmitted onto said tissue material;
generating a signal based on said light energy detected by said detector; and
analyzing said signal in order to produce said data.

23. The data of claim 22, wherein the act of analyzing said signal comprises the act of processing at least a portion of said signal using a digital signal processor.

24. The data of claim 23, wherein the act of processing said signal comprises performing a series of mathematical operations on said signal using said digital signal processor.

25. The data of claim 24, further comprising the act of shielding said detector against electromagnetic interference using a Faraday shield.

26. The optical probe of claim 1 wherein said first attenuation property comprises absorption.

27. The optical probe of claim 1, wherein said first area is positioned to interact with the ambient light energy.

28. The optical probe of claim 1, wherein said first area is positioned to interact with the light energy which emitted from the light source and which did not transmit through the tissue material.

29. The optical probe of claim 1, wherein said first area is positioned to interact with the ambient light energy and the light energy which emitted from the light source and which did not transmit through the tissue material.

30. The optical probe of claim 1, wherein said second attenuation property comprises reflectance.

31. The optical probe of claim 1, wherein said second area is positioned to interact with the light energy which emitted from the light source and which transmitted through the tissue material.

32. The optical probe of claim 1, wherein said first attenuation property comprises absorption and said seocnd attenuation property comprises reflectance.

33. The optical probe of claim 1, wherein said second area surrounds at least one of said first and second apertures.

34. The optical probe of claim 1, wherein the first support surface includes the first area and the second area.

35. The optical probe of claim 34, wherein the second support surface includes a third area having the first attenuation property and a fourth area having the second attenuation property.

36. The optical probe of claim 1, wherein the second support surface includes the first area and the second area.

* * * * *